United States Patent
Nishizawa et al.

(10) Patent No.: US 9,617,649 B2
(45) Date of Patent: Apr. 11, 2017

(54) POROUS STRUCTURE PROVIDED WITH A PATTERN THAT IS COMPOSED OF CONDUCTIVE POLYMER AND METHOD OF MANUFACTURING THE SAME

(75) Inventors: Matsuhiko Nishizawa, Sendai (JP); Soichiro Sekine, Sendai (JP); Yuichiro Ido, Sendai (JP)

(73) Assignee: TOHOKU UNIVERSITY, Miyagi (JP)

( * ) Notice: Subject to any disclaimer, the term of this patent is extended or adjusted under 35 U.S.C. 154(b) by 642 days.

(21) Appl. No.: 13/637,494

(22) PCT Filed: Mar. 25, 2011

(86) PCT No.: PCT/JP2011/057420
§ 371 (c)(1),
(2), (4) Date: Jan. 31, 2013

(87) PCT Pub. No.: WO2011/118800
PCT Pub. Date: Sep. 29, 2011

(65) Prior Publication Data
US 2013/0126220 A1    May 23, 2013

(30) Foreign Application Priority Data
Mar. 26, 2010   (JP) .................... 2010-073820

(51) Int. Cl.
*C25D 9/02*    (2006.01)
*A61N 1/04*    (2006.01)
(Continued)

(52) U.S. Cl.
CPC ............ *C25D 9/02* (2013.01); *A61N 1/0496* (2013.01); *H05K 1/03* (2013.01); *C09D 5/4407* (2013.01);
(Continued)

(58) Field of Classification Search
CPC ...... C25D 9/02; C09D 5/4476; C09D 5/4407; A61N 1/0496; H05K 1/03; H05K 1/0313; H05K 1/0353
See application file for complete search history.

(56) References Cited

U.S. PATENT DOCUMENTS

| 2002/0134980 A1* | 9/2002 | Armgarth et al. ............... 257/59 |
| 2007/0060815 A1* | 3/2007 | Martin ................. A61B 5/0408 600/372 |
| 2007/0085061 A1* | 4/2007 | Elder et al. ................... 252/500 |

FOREIGN PATENT DOCUMENTS

| JP | 11-290286 A | 10/1999 |
| JP | 2000-505249 A | 4/2000 |

(Continued)

OTHER PUBLICATIONS

D. Kim et al, "Conducting polymers grown in hydrogel scaffolds coated on neural prosthetic devices", Wiley Periodicals, Inc., pp. 577-585, 2004.

(Continued)

*Primary Examiner* — Ling Choi
*Assistant Examiner* — David L Miller
(74) *Attorney, Agent, or Firm* — Westerman, Hattori, Daniels & Adrian, LLP

(57) ABSTRACT

A porous structure (1) provided with a pattern that is composed of a conductive polymer, which comprises a porous body (2) and a pattern (3) that is composed of a conductive polymer and arranged on the porous body (2). The porous body (2) is preferably a gel, and a dopant may be added to the pattern (3) that is composed of a conductive polymer. If an agarose gel is used as the gel (2) and a PEDOT electrode (3A) is used as the pattern (3) that is composed of a conductive polymer in the porous structure (1) which is provided with the pattern (3) that is composed of a conductive polymer, the porous structure (1) can be used (Continued)

as an electrode for cell stimulation. The porous structure (1) provided with the pattern (3) that is composed of a conductive polymer can be produced by an electropolymerization method.

13 Claims, 18 Drawing Sheets

(51) Int. Cl.
*C09D 5/44* (2006.01)
*H05K 1/03* (2006.01)

(52) U.S. Cl.
CPC ......... *C09D 5/4476* (2013.01); *H05K 1/0313* (2013.01); *H05K 1/0353* (2013.01)

(56) References Cited

FOREIGN PATENT DOCUMENTS

| JP | 2001-000406 A | 1/2001 |
|----|---------------|--------|
| JP | 2001-160318 A | 6/2001 |
| JP | 2003-346554 A | 12/2003 |
| JP | 2005-304212 A | 10/2005 |
| JP | 2007-534162 A | 11/2007 |
| JP | 2009-506836 A | 2/2009 |
| JP | 2010-148691 A | 7/2010 |

OTHER PUBLICATIONS

U. Zschieschang et al, "Flexible Organic Circuits with Printed Gate Electrodes**", Advanced Materials,15, No. 14, Jul. 17, 2003, pp. 1147-1151, Wiley-VCH Verlag GmbH & Co. KGaA, Weinheim.

W. Schuhmann et al, "Pulse technique for the electrochemical deposition of polymer films on electrode surfaces", Biosensors & Bioelectronics vol. 12, No. 12, pp. 1157-1167, (1997).

J. Yu et al, "Chemically amplified photolithography of a conjugated polymer", Chem. Commun., pp. 1503-1504, 1998.

Z. Bao et al, "Printable organic and polymeric semiconducting materials and devices", J. Mater. Chem., pp. 1895-1904, 1999.

B. Chen et al, "All-polymer RC filter circuits fabricated with inkjet printing technology", Solid-State Electronics 47, pp. 841-847, 2003, Elsevier Science Ltd.

W. S. Beh et al, "Formation of Patterned Microstructures of Conducting Polymers by Soft Lithography, and Application in Microelectronic Device Fabrication", Advance Materials 11, No. 12, Wiley-VCH Verlag GmbH, D-69469 Weinheim, pp. 1038-1041, 1999.

T. Granlund et al, "Patterning of Polymer Light-Emitting Diodes with Soft Lithography", Advanced Materials, 12, No. 4, Wiley-VCH Verlag GmbH, D-69469 Weinheim, pp. 269-273, 2000.

B. W. Maynor et al, "Direct-Writing of Polymer Nanostructures: Poly(thiophene) Nanowires on Semiconducting and Insulating Surfaces", JACS Communications, vol. 124, No. 4, pp. 522-523, 2002.

International Search Report for PCT/JP2011/057420, mailing date of Jun. 14, 2011.

* cited by examiner

FIG. 5
(A)
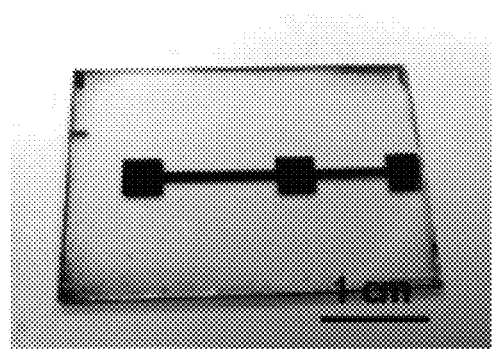
(B)
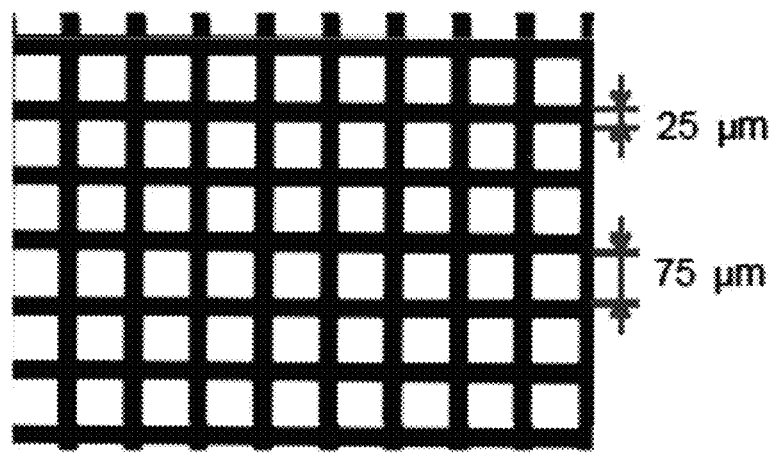

FIG. 8
(A) 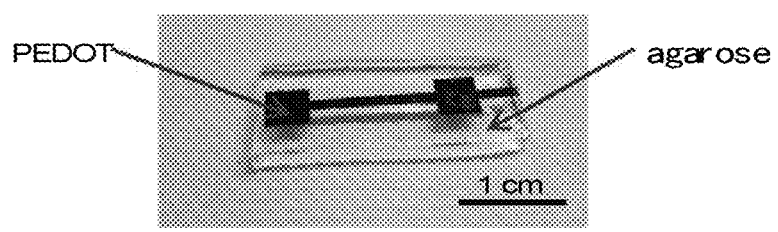
(B) 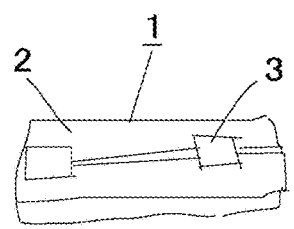

FIG. 9
(A)
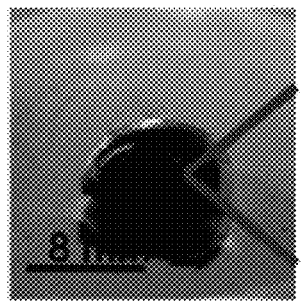
(B)
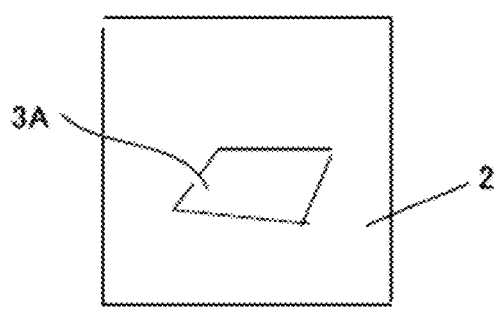
(C)
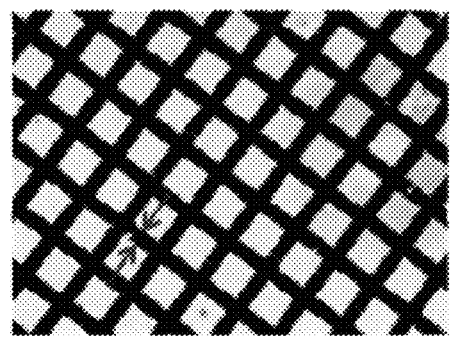
Line Width=25 μm

FIG. 11
(A)
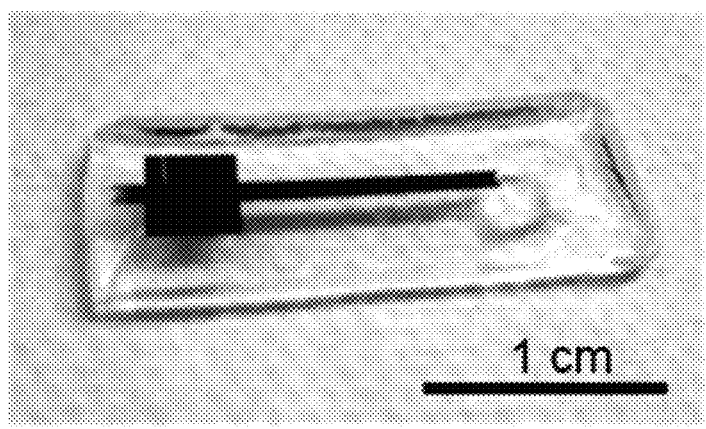
(B)
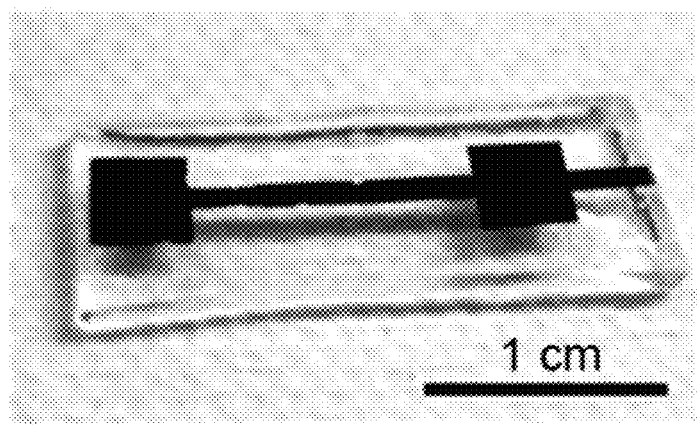

FIG. 16
(A)
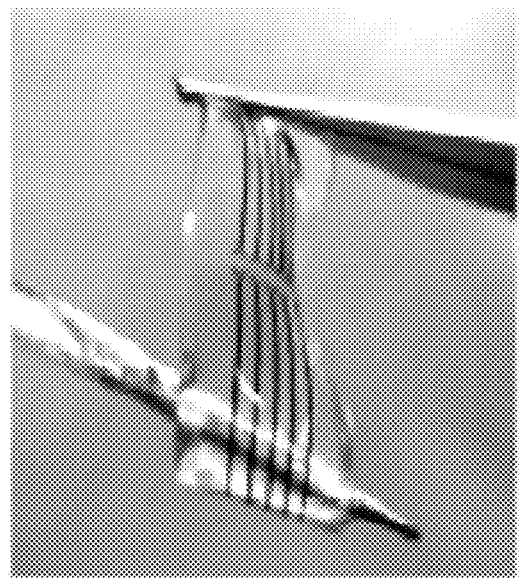
(B)
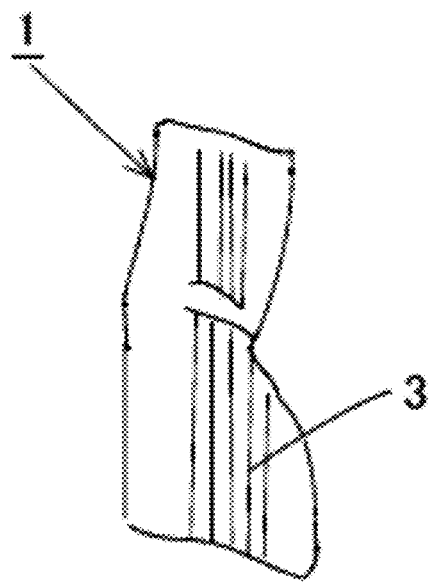

FIG. 17
(A) 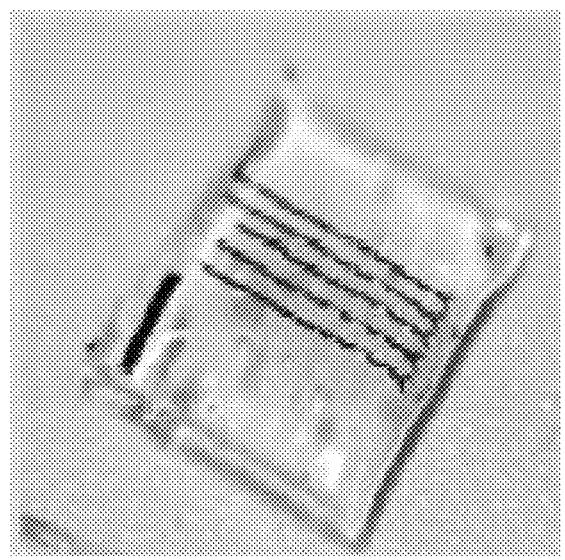
(B) 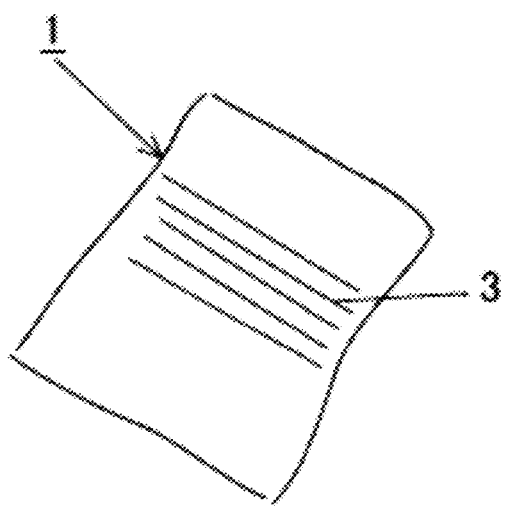

FIG. 18
(A) 
(B) 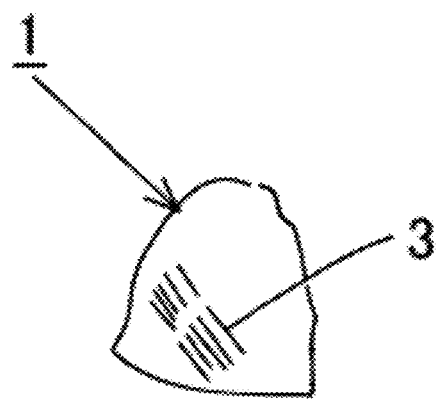

POROUS STRUCTURE PROVIDED WITH A PATTERN THAT IS COMPOSED OF CONDUCTIVE POLYMER AND METHOD OF MANUFACTURING THE SAME

TECHNICAL FIELD

The present invention relates to a porous structure provided with a pattern that is composed of conductive polymer and a method for producing the same. In particular, the present invention relates to a porous structure in which an electrode for example is formed as a pattern that is composed of conductive polymer on a porous body and a method of manufactuiring the same.

BACKGROUND ART

In recent years, researches have been actively performed on a device for directly controlling a living organism system such as an implanted medical apparatus or a nerve stimulation electrode. However, an interface between the artificial device and the living organism system has various problems caused by a difference in constituting materials and a significant difference in the physical characteristic and the chemical characteristic. For example, when a metal electrode is used to apply an electrical stimulation to cells, the cells are undesirably damaged by the toxicity of eluted metal ions or bubbles caused by electrolyzation.

In order to reduce the problems as described above, it is important to establish an interface by such material that can provide efficient information transmission and that is highly compatible with a living organism (i.e., a bio interface). Materials compatible with a living organism include conductive polymer that is highly flexible and that has a high interfacial capacity. For example, cells can be electrically stimulated efficiently by coating a metal surface with conductive polymer compatible with a living organism.

If hard material such as metal or glass is used around cells involved in expansion and contraction such as muscle cells, the material not only limits the expansion and contraction but also causes a difficulty in the adhesion of the cells to the material due to expansion and contraction.

Due to this reason, the artificial device has been required to be composed of flexible material closer to a living organism tissue. Such material exemplarily includes hydrogel such as agarose gel, fibrin gel, or collagen gel. These hydrogels have a solid state, can retain a large amount of water, and are flexible. Thus, applications of these hydrogels for a solid electrolyte have been developed (see Patent References 1 to 3). Some hydrogels are highly compatible with a living organism and have been used for a cell culture substrate and a bioreactor for example.

Techniques to perform the electropolymerization of conductive polymer at the surface or the interior of porous material such as hydrogel includes polypyrrole electropolymerization carried out in the University of Michigan (see Nonpatent Reference 1). According to Nonpatent Reference 1, polypyrrole polymerized on an electrode covered with gel starts growing from the gel fibers in a three-dimensional manner, demonstrating an improved performance of a nerve stimulation electrode. However, in the case of Nonpatent Reference 1, the gel-covered electrode, the gel, and the conductive polymer are structured in an integrated manner, thus failing to provide an elastic electrode.

Regarding the patterning of conductive polymer, many methods have been suggested, including lithography using resist (see Patent Reference 4), a micro contact printing method (see Nonpatent Reference 2), scanning electrochemical microscopy (see Nonpatent Reference 3), photochemical reaction method (see Nonpatent Reference 4), screen printing (see Nonpatent Reference 5), ink jet printing (see Patent Reference 5 and Nonpatent Reference 6), a capillary method (see Nonpatent Reference 7), a transfer method (see Nonpatent Reference 8), and a clip pen method (see Nonpatent Reference 9). All of these techniques perform patterning of conductive polymer on a rigid substrate such as glass and thus cannot be used for aqueous porous material such as gel.

The material that is aqueous porous material such as gel and that is porous material including electrolyte includes gel material such as agarose gel or fibrin gel. Such electrolyte gel is highly aqueous. Thus, in the case of an existing known technique such as a dispersion liquid coating by an inkjet printer, it is difficult to realize the pattern printing of such material.

PRIOR TECHNICAL REFERENCE

Patent Reference

Patent Reference 1: JP1999-290286 A
Patent Reference 2: JP2001-406 A
Patent Reference 3: JP 2003-346554 A
Patent Reference 4: JP 2000-505249 A1
Patent Reference 5: JP 2007-534162 A1

Nonpatent Reference

Nonpatent Reference 1: Dong-Hwan Kim, David C. Martin, J, Biomed Mater Res, 2004
Nonpatent Reference 2: U. Zschieschang, H. Klauk, Adv. Mater, 15, 1147, 2003
Nonpatent Reference 3: W. Schuhmann, C. Kranz, Biosensors & Bioelectronics, 12, 1997
Nonpatent Reference 4: J. Yu, Y. Abley, C. Yang, Chem. Commun, 1503, 1998
Nonpatent Reference 5: Z. Bao, J. A. Rogers, H. E. Katz, J. Mater. Chem., 9, 1895, 1999
Nonpatent Reference 6: B. Chen, T. Cui, Y. Liu, K. Varahrmanyan, Solid-state Electron. 47, 841, 2003
Nonpatent Reference 7: W. S. Beh, I. T. Kim, D. Qin, Y. Xia, Adv. Mater, II, 1038, 1999
Nonpatent Reference 8: T. Granlund, T. Nyberg, L. S. Roman, M. Svensson, Adv. Mater, 12, 269, 2000
Nonpatent Reference 9: B. W. Maynor, S. F. Filocamo, M. W. Grinstaff, J. Am. Chem. SoC, 124(4), 522, 2002
Nonpatent Reference 10: Fukyuuban Geru Handobukku, NTS, 2003

SUMMARY OF THE INVENTION

Problem to be Solved by the Invention

In the case of the existing conventional patterning method of conductive polymer, the method can be applied only to a dry and rigid substrate such as glass. Thus, this conventional method could not realize the electrode formation in aqueous porous material.

In view of the above, it is an objective of the present invention to provide a porous structure provided with a pattern that is composed of conductive polymer and a method of manufacturing the same.

Means for Solving the Problem

In order to achieve the first objective, a porous structure provided with a pattern that is composed of conductive polymer of the present invention includes: a porous body; and a pattern that is provided on this porous body and that is composed of conductive polymer.

In the configuration, the porous body is preferably gel. The gel has a water content percentage of preferably 70 to 99%. This gel may be composed of hydrogel. The gel is preferably any of agarose gel, collagen, glucomannan, polyacrylamide, polyvinyl alcohol, polyhydroxyethyl methacrylate, or polyvinylpyrrolidone. The conductive polymer may be any of PEDOT, polypyrrole, or polyacetylene. The conductive polymer is preferably added with a dopant. The conductive polymer has a conductivity of preferably 10 S/cm or more.

In order to achieve the second objective, a method of manufactuiring a porous structure provided with a pattern that is composed of conductive polymer of the present invention includes: a step of forming an electrode pattern functioning as a working electrode; a step of inserting a working electrode pattern to electrolyte liquid including raw material of conductive polymer; a step of placing a porous body on the working electrode pattern; a step of performing electropolymerization for a predetermined time to deposit a pattern that is composed of the conductive polymer between the porous body and the electrode pattern; and a step of peeling the porous body from the electrode pattern to thereby provide the porous structure provided with the pattern that is composed of conductive polymer.

In the configuration, the raw material of conductive polymer is preferably composed of monomer of conductive polymer. Preferably, the electropolymerization is followed by at least one or more applications of negative and positive voltages to the working electrode in an alternate manner.

The electrolyte liquid further includes a dopant. This dopant may be $KNO_3$.

The pattern that is composed of conductive polymer has the minimum line width that is preferably wider than the minimum line width of the electrode pattern functioning as a working electrode by 1 μm to 10 μm.

Effects of the Invention

According to a porous structure provided with a pattern that is composed of conductive polymer of the present invention, a pattern that is composed of conductive polymer can be formed on the surface of a porous body such as soft gel.

According to the method of the present invention of manufactuiring a porous structure provided with a pattern that is composed of conductive polymer, electropolymerization can be used to form a pattern that is composed of conductive polymer on the surface of a porous body such as soft gel. The electropolymerization and the dopant doping and undoping to the conductive polymer can be controlled by electricity thus achieving the formation of a flexible electrode on the surface of gel for example without requiring substrate modification or a special apparatus.

BRIEF DESCRIPTION OF THE DRAWINGS

In the drawings.

FIG. 5 illustrates an example of an electrode pattern of a potentiostat working electrode (WE) wherein (A) illustrates a line pattern and (B) illustrates a grid-like pattern;

FIG. 8(A) illustrates an optical image of the porous structure 1 including a line pattern composed of conductive polymer of Embodiment 1 formed through three cycles of the application of positive and negative voltages after electropolymerization and (B) is a schematic view of the image.

FIG. 9(A) illustrates an expanded optical image of a grid-like line pattern composed of conductive polymer of FIG. 8, and (B) is a schematic view of the image and (C) is an expanded optical image of (A);

FIG. 11 illustrate a porous structure provided with a pattern that is composed of conductive polymer wherein (A) illustrates the transfer where the electropolymerization time is 10 minutes and (B) illustrates the transfer where the electropolymerization time is 60 minutes;

FIG. 16(A) illustrates an optical image of a porous structure provided with a pattern that is composed of conductive polymer of Embodiment 2 and (B) is a schematic view of the image.

FIG. 17(A) illustrates an optical image of a porous structure provided with a pattern that is composed of conductive polymer of Embodiment 3 and (B) is a schematic view of the image; and FIG. 18(A) illustrates an optical image of a porous structure provided with a pattern that is composed of conductive polymer of Embodiment 4 and (B) is a schematic view of the image.

DESCRIPTION OF CODES

Figure 1:
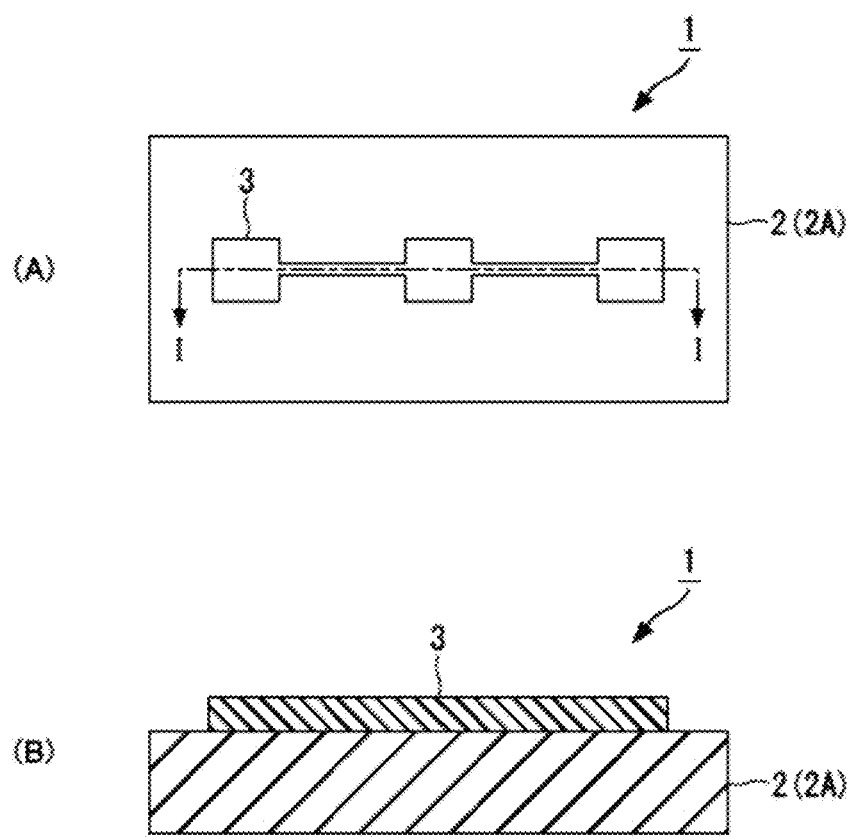
FIG. 1 illustrates the structure of a porous structure provided with a pattern that is composed of conductive polymer according to the first embodiment of the present invention wherein (A) is a top view and (B) is a cross-sectional view taken along the line I-I of (A)

1: Porous structure provided with pattern that is composed of conductive polymer
2: Porous body
3: Pattern that is composed of conductive polymer
3A: PEDOT electrode 10: Electropolymerization apparatus
11: Electrolyte liquid
11A: Electrolyte aqueous solution
12: Container
13: Working electrode
14: Counter electrode
15: Reference electrode
17: Potentiostat
19: Substrate
21: Ammeter
22: DC power source
23: Voltmeter
25: Working electrode pattern
27: Gel peeling power source
30: Myotube cell gel sheet
32: Acrylic plate
33: Pt electrode
34: Electrical stimulation apparatus thesized gel 2 (i.e., synthesized gel) contains water. Thus, the term "gel 2" generally means the hydrogel 2A that is water medium. Human bodies are also composed of 60% or more water and thus can be generally assumed as the hydrogel 2A. Thus, the hydrogel 2A has been recognized as material highly compatible with a living organism. In fact, many of the hydrogel 2A is derived from a living organism. For example, seaweed-derived agar media has been used for 100 years or more.

Hydrogel used for the porous body 2 include agarose gel represented by the following chemical formula (1). The porous material as described above may have a water content percentage of 70 to 99% for example. The porous material as described above having a water content percentage of 70% or less is not preferred because the diffusion of raw material of conductive polymer or dopant is inhibited. The porous material having a higher water content percentage on the other hand is desirable because a higher water content percentage provides a higher compatibility with a living organism. However, a water content percentage of 99% or more makes it difficult to retain the structure.

[Chemical formula 1]

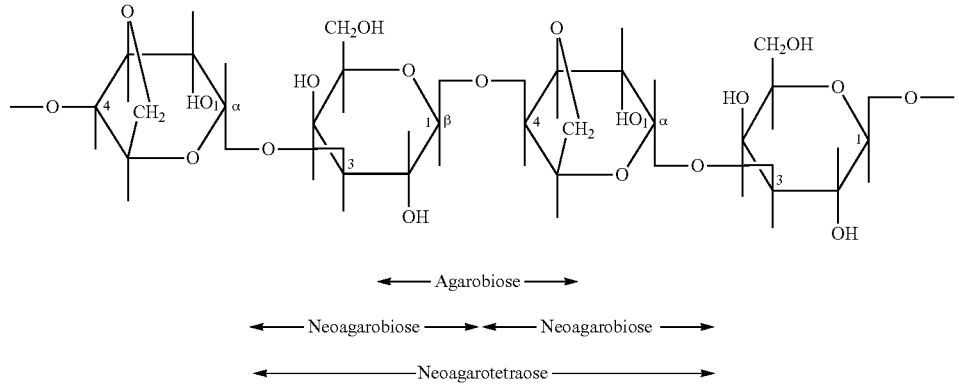

MODE FOR CARRYING OUT THE INVENTION

The following section will describe an embodiment of the present invention with reference to the drawings.

First Embodiment

The following section will describe, as the first embodiment, a porous structure provided with a pattern that is composed of conductive polymer.

FIG. 1 illustrate the structure of a porous structure 1 including a pattern 3 that is composed of conductive polymer according to the first embodiment of the present invention wherein (A) is a top view and (B) is a cross-sectional view taken along the line I-I of (A).

As shown in FIG. 1(A), the porous structure 1 provided with the pattern 3 that is composed of conductive polymer of the present invention is comprising: a porous body 2; and the pattern 3 that is composed of conductive polymer and provided on the porous body 2. The porous body 2 is composed of porous material such as gel or hydrogel.

The gel 2A is defined as "polymer having a three-dimensional mesh structure that is insoluble in any solvent and the swelling material thereof. The mesh of the gel formed due to a change in the temperature or pH can suppress the leakage of solvent. Thus, the gel can retain a great amount of solvent at the interior thereof (see Non-patent Reference 10). Such gel that retains water as solvent is called hydrogel 2A and shows a very high water absorbability. Many currently-existing natural substances and syn- The agarose gel 2A is neutral polysaccharide that is a main component of agar and that has a very-high gelatinization force. As shown in the chemical formula (1), the agarose gel 2A has a structure composed of the repetition of D-galactose and 3,6-anhydro-L-galactose.

The agarose gel 2A can be easily prepared by the procedure as described below. Specifically, agarose powders are added to ion-exchange water to prepare agarose solution having a predetermined concentration. Then, the agarose solution is heated until the agarose solution boils to achieve a sol-like status. Then, this sol-like solution is allowed to flow in a mold and is left in a static manner and the solution is cooled at a room temperature for example until the solution turns to gel.

The porous body 2 may be composed of such gel including, in addition to the agarose gel 2A, collagen, glucomannan, polyacrylamide, polyvinyl alcohol, or soft contact lens gel for example. The soft contact lens gel may include polyhydroxyethyl methacrylate (Poly-HEMA) or polyvinylpyrrolidone for example.

The conductive polymer used for the pattern 3 that is composed of conductive polymer may be, for example, polyacetylene represented by the following chemical formula (2), polypyrrole represented by the following chemical formula (3), or poly(ethylenedioxy)thiophene (hereinafter referred to as PEDOT) represented by the following chemical formula (4). In addition, the conductive polymer may include polythiophene, polybithiophene, polyisothiophene, polydodecylthiophene, polyisonaphtothiophene, poly-3- hexylthiophene, polyaniline, polyisothianaphthene, polythiazyl, polyphenylene, polyfluorene, polydiacetylene, polyacene, polyparaphenylene, polythienylene vinylene, polyphenylene sulfide for example.

[Chemical formula 2]

[Chemical formula 3]

[Chemical formula 4]

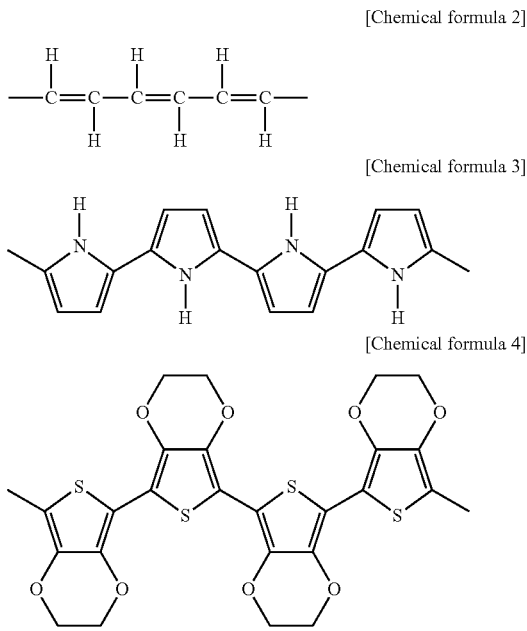

In order to control the conductivity and conductivity type of the conductive polymer, the impurities (hereinafter referred to as dopant) may be added further to the conductive polymer. Such dopant may be polystyrene sulfonic acid (hereinafter referred to as PSS) represented by the following chemical formula (5) or potassium nitrate ($KNO_3$). In addition, such dopant including halogens (e.g., Br, I, CO, Lewis acid (e.g., $BF_3$, $PF_5$), protic acid (e.g., $HNO_3$, $H_2SO_4$), transition metal halide (e.g., $FeCl_3$, $MoCl_5$), alkali metal (e.g., Li, Na), organic substance (e.g., amino acid, nucleic acid, surface-activating agent, pigment, alkylammonium ion, chloranil, tetracyanoethylene, 7.7.8.8.-tetracyanoquinodimethane) for example may be added to the conductive polymer.

[Chemical formula 5]

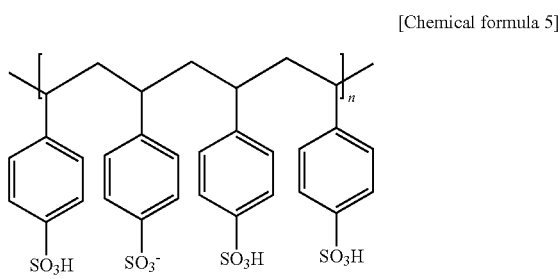

The pattern 3 that is composed of conductive polymer can be a linear pattern, a two-dimensional pattern, or a three-dimensional pattern.

Such conductive polymer can be used that has a conductivity of 10 S (siemens)/cm or more depending on a desired resistance value of the pattern 3. Conductive polymer having a conductivity lower than 10 S/cm is not preferred because a high resistance is caused in the pattern 3 that is composed of conductive polymer. On the other hand, the conductive polymer having a higher conductivity is acceptable because pattern 3 has a reduced resistance.

The porous structure 1 including the pattern 3 that is composed of conductive polymer of the present invention is configured so that the pattern 3 that is composed of conductive polymer is placed on the porous body 2 such as gel composed of only organic substance. The pattern 3 that is composed of conductive polymer can function as an electrode. Specifically, when the gel 2 has thereon the pattern 3 that is composed of conductive polymer, a flexible electrode highly compatible with a living organism can be provided.

Furthermore, the porous structure 1 including the pattern 3 that is composed of conductive polymer of the present invention also can be used for a living organism interface for various devices in the biomedical field. Applications using such material compatible with a living organism or using a reversible biochemical doping include an electrode pad, a cell culture base, a biosensor, a polymer actuator and a cell stimulation system that is stretchable in synchronization with cells or tissue. The pattern 3 that is composed of conductive polymer can be used as an electrode pad compatible with a living organism that can be used, for example, as an electrode to measure brain waves or an electrocardiogram. Since this electrode pad 1 can be provided as a very fine micropattern, for example the resolution can be improved in the brain wave measurement. Such applications also include the field of metal-free organic electronics using the high interfacial capacity and flexibility enabled by the conductive polymer and techniques to prepare various batteries and fuel cells.

Second Embodiment

The following section will describe the second embodiment for a method of manufacturing the porous structure 1 including the pattern 3 that is composed of conductive polymer.

Figure 2:
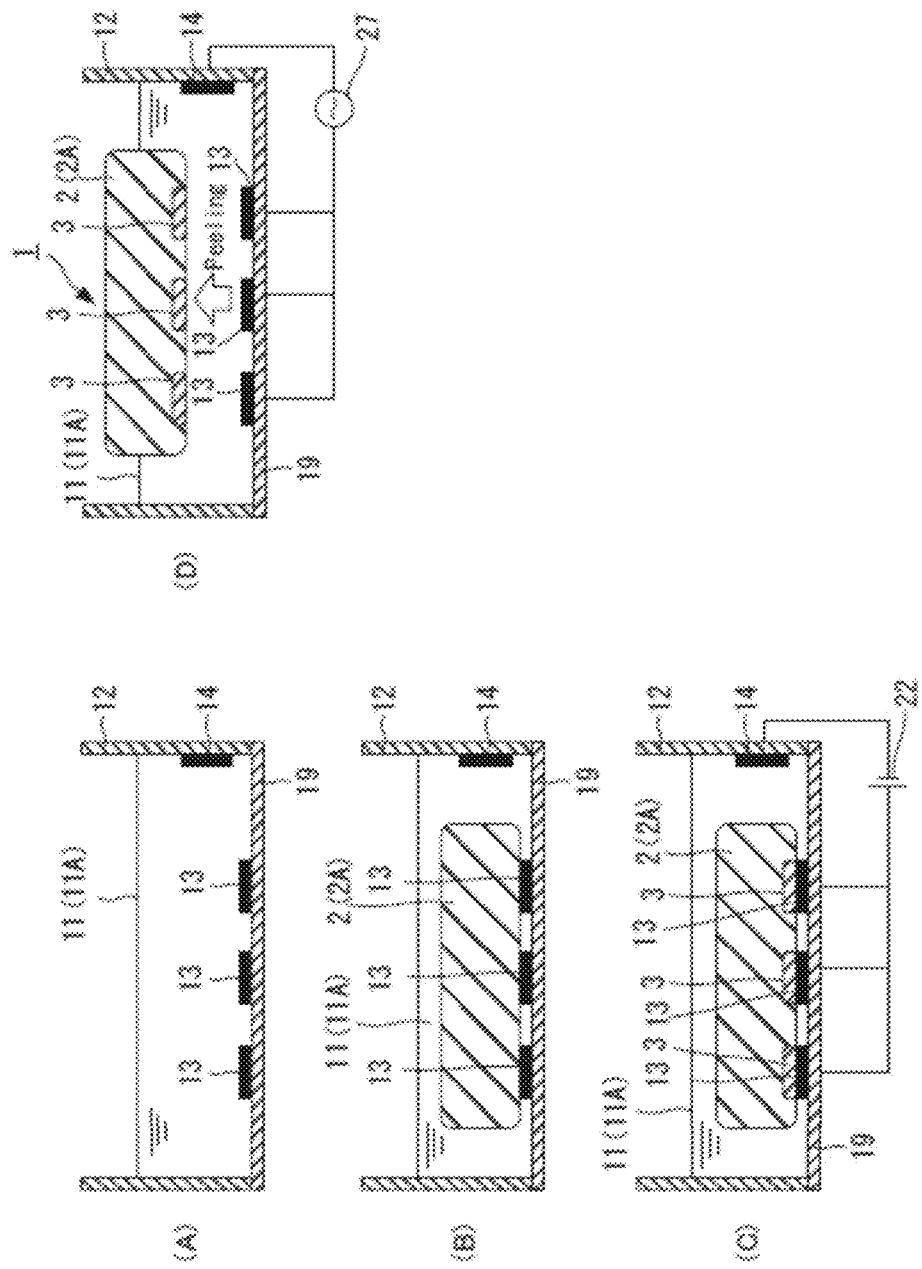
FIG. 2 is a schematic view sequentially illustrating one example of a method of manufacturing a porous structure provided with a pattern that is composed of conductive polymer.
Figure 3:
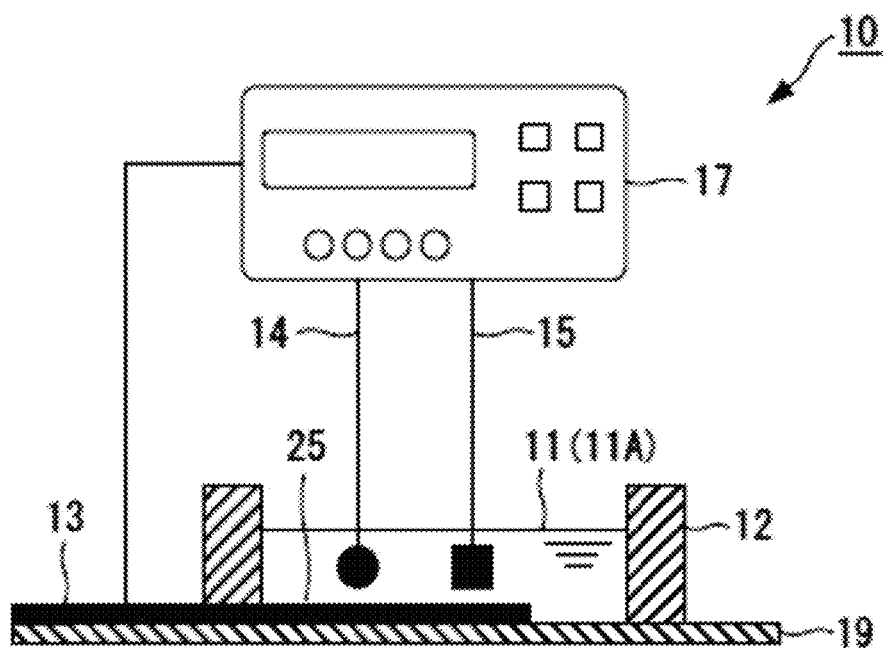
FIG. 3 is a schematic view illustrating the configuration of an electropolymerization apparatus used in electropolymerization.
Figure 4:
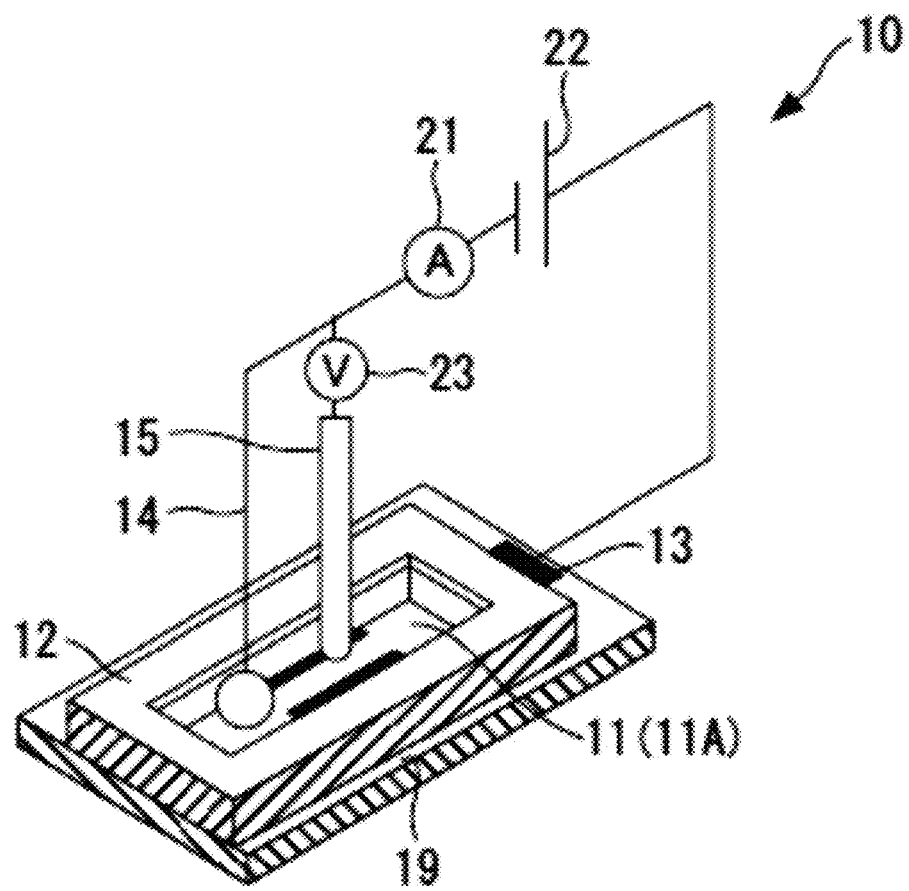
FIG. 4 is a schematic view illustrating the electrode configuration of the electropolymerization apparatus.

FIG. 2 is a schematic view illustrating one example of a method of manufacturing the porous structure 1 including the pattern 3 that is composed of conductive polymer in a sequential manner. FIG. 3 is a schematic view illustrating the configuration of an electropolymerization apparatus 10 used for electropolymerization. FIG. 4 is a schematic view illustrating the electrode configuration of the electropolymerization apparatus 10.

As shown in FIG. 2A, electrolyte liquid 11 including conductive polymer is placed in a container 12. The conductive polymer in the electrolyte liquid 11 may be raw material of conductive polymer. The raw material of conductive polymer may be a monomer of conductive polymer. The monomer is also called as a unit monomer and is used as a unit constituting the basic structure of conductive polymer. The electrolyte liquid 11 is electrolyte aqueous solution 11A for example. The impurities (which is called a dopant) may be added to the electrolyte liquid 11 including conductive polymer for the doping of the conductive polymer. This electrolyte liquid 11 is configured so that a so-called potentiostat 17 using three electrodes is used to apply a voltage to the electrolyte liquid 11. The following description will be made based on the assumption that the electrolyte liquid 11 is the electrolyte aqueous solution 11A.

As shown in FIG. 3, the electropolymerization apparatus 10 is constructed including: a container 12 for storing the electrolyte aqueous solution 11; a working electrode (WE) 13 inserted to the electrolyte aqueous solution 11; a counter electrode (CE) 14 and a reference electrode (RE) 15; and a potentiostat 17 for applying a voltage to the working electrode 13, the counter electrode 14, and the reference electrode 15. The container 12 also may be provided on a substrate 19 thereon on which the working electrode 13 is formed.

As shown in FIG. 4, in the electropolymerization apparatus 10, the working electrode 13 and the counter electrode 14 are connected to a DC power source 22 via an ammeter 21. An electrolysis voltage is applied to the electrolyte aqueous solution 11A. In the shown case, a positive voltage is applied to the working electrode 13 and a negative voltage is applied to the counter electrode 14. A reference electrode 15 is connected to the counter electrode 14 via a voltmeter 23. Specifically, the reference electrode 15 is connected to the potentiostat 17. That is, the reference electrode 15 is connected to potentiostat 17 and the potential of the working electrode 13 is controlled by based on the reference electrode 15 as a reference. During this control, the current flowing in the working electrode 13 is measured by the ammeter 21. This current is electrolysis current flowing in the electrolyte aqueous solution 11A.

A predetermined pattern which will be formed on the gel 2 is formed on an electrode pattern 25 of the working electrode. FIG. 5 illustrates an example of the electrode pattern 25 of the working electrode 13 of the potentiostat, (A) illustrates a line pattern and (B) illustrates a grid-like pattern.

Next, after the step as shown in FIG. 2A, the gel as the porous body 2 is inserted to the electrolyte aqueous solution 11A as shown in FIG. 2B.

Then, as shown in FIG. 2C, a voltage is applied to the electrolyte aqueous solution 11A to perform electropolymerization, thereby forming the pattern 3 consisting of conductive polymer between the porous body 2 and the working electrode 13. After a predetermined electropolymerization time has passed (i.e., when the pattern 3 that is composed of conductive polymer has a predetermined thickness), the voltage application to the electrolyte aqueous solution 11A is stopped. By peeling the gel 2 from the working electrode 13 while maintaining this condition, the porous structure 1 including the pattern 3 that is composed of conductive polymer can be manufactured. Specifically, the electrode pattern 25 of the working electrode 13 is transferred onto the surface of the gel 2 as the pattern 3 that is composed of conductive polymer.

The electrode pattern 25 of the working electrode 13 is transferred onto the porous structure 1 including the pattern 3 that is composed of conductive polymer of the present invention. Thus, in principle, the minimum line width of the electrode pattern 25 of the working electrode 13 (also called the minimum line width) equals to the minimum line width of the pattern 3 that is composed of conductive polymer. The minimum line width of the electrode pattern 25 of the working electrode 13 is about 10 nm when prepared by an electron beam exposure for example. Thus, this is a one of the featutes using electropolymerization which can also provide the control of the line width of the pattern 3 of the conductive polymer patterned by the electrode pattern 25 of the working electrode 13. The line width of the patterned conductive polymer 3 (i.e., line width) can have an arbitrary value of 10 μm or more when the electrode pattern 25 of the working electrode 13 has the minimum line width of 10 μm.

When the electrode pattern 25 of the working electrode 13 is transferred onto the surface of the gel 2, this transfer pattern (i.e., the pattern 3 that is composed of conductive polymer) can have such a line width that is larger by about 1 μm to 10 μm than the line width of the electrode pattern 25 of the working electrode 13 formed on the substrate 19. Thus, this transfer pattern can be a wide pattern. When the pattern 3 that is composed of conductive polymer has a line width of 1 μm or less, such a line width is not preferred because the pattern 3 that is composed of conductive polymer has a reduced thickness. On the other hand, when the pattern 3 that is composed of conductive polymer has a line width of 10 μm or more such a line width is not preferred because the pattern 3 that is composed of conductive polymer has an increased thickness, thereby causing a declined flexibility.

A film thickness of the pattern 3 that is composed of conductive polymer formed on the gel 2 can be controlled by an amount of charge (unit: coulomb) by using the electropolymerization. This amount of charge is calculated based on the product (I×t) of the electrolysis current (I) flowing in the ammeter 21 and the time (t) during which the electrolysis current (I) flows. Specifically, the electropolymerization has a featute that it can be controlled the film thickness of the pattern 3 that is composed of conductive polymer by electricity. Furthermore, since the electropolymerization can realize the selective film formation only on the working electrode 13, the electropolymerization is a useful method for coating in particular.

After the completion of the electropolymerization as shown in FIG. 2(C), since the electropolymerized conductive polymer is also deposited in the interior of the gel 2 there may be a case that the gel 2 is strongly adhered to the working electrode 13 formed on the substrate 19 via the pattern 3 that is composed of conductive polymer. In this case, the pattern 3 is composed of conductive polymer is formed in the interior of the gel 2. Thus, the peeling of such gel 2 may cause the gel 2 to be partially remained on the working electrode 13.

Specifically, the gel 2 cannot be completely peeled from the working electrode 13. The electropolymerized pattern 3 that is composed of conductive polymer is also deposited in the interior of the gel 2. Thus, this deposition status is exaggerated in FIG. 2(C).

In order to be able to easily peel the gel 2 from the working electrode 13, as shown in FIG. 2(D), gel peeling power source 27 is applied between the working electrode 13 and the counter electrode 14. This gel peeling power source 27 can alternately generate positive and negative voltages for a predetermined time.

Figure 6:
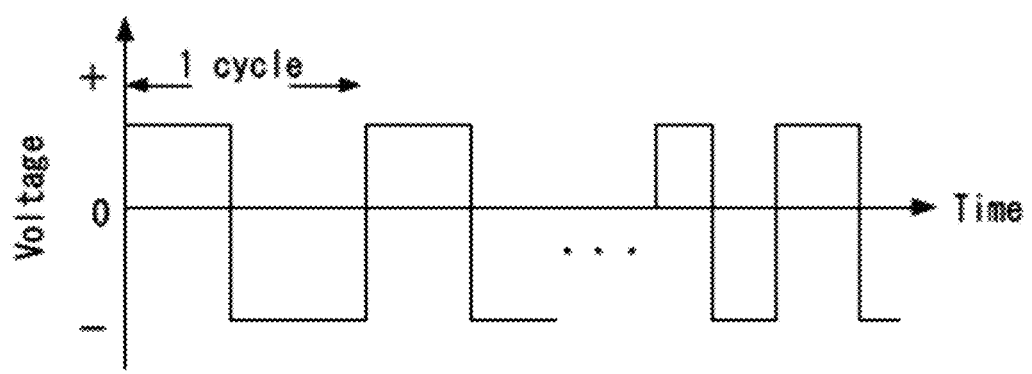
FIG. 6 illustrates the waveform of a voltage applied from a gel peeling power source to a working electrode.

FIG. 6 illustrates a voltage waveform applied from the gel peeling power source 27 to the working electrode 13. In FIG. 6, the horizontal axis shows time and the vertical axis shows a voltage applied to the working electrode 13. Positive and negative voltages are determined based on the reference electrode 15. As shown in FIG. 6, with an assumption that the time required for applying positive and negative voltages is one cycle, AC voltage can be applied to the working electrode 13 for a predetermined number of cycles.

Figure 7:
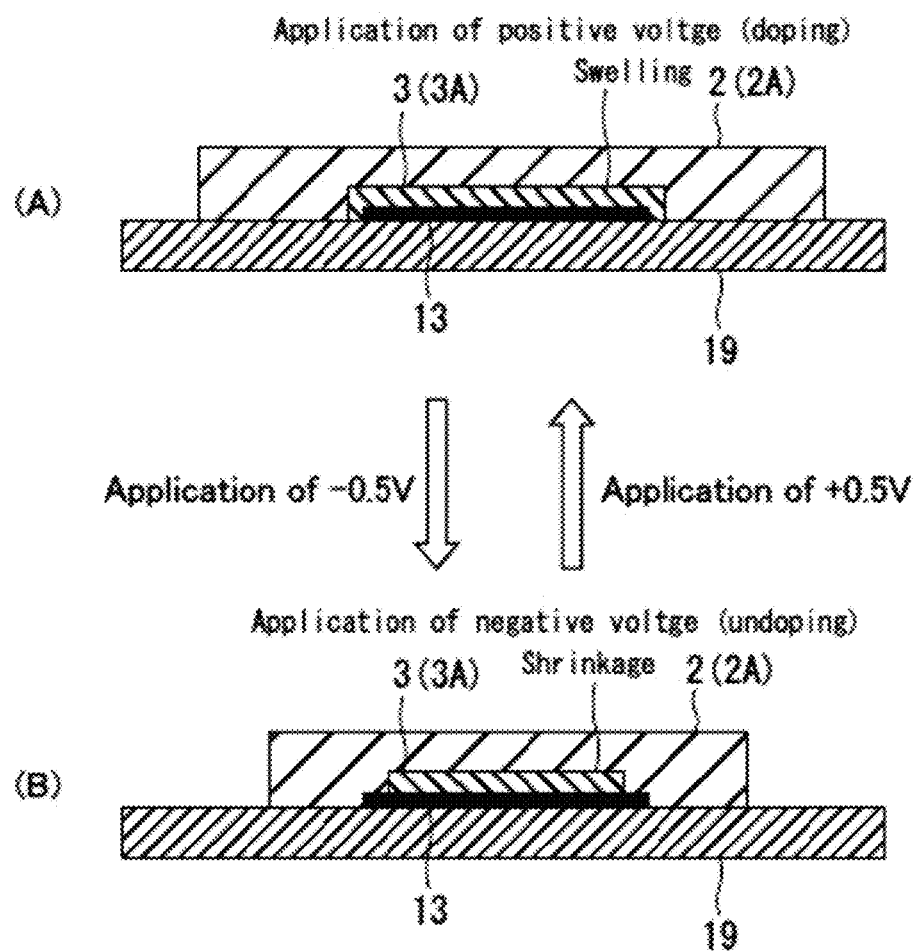
FIG. 7 illustrates the cross section of a working electrode, a pattern that is composed of conductive polymer, and gel when a voltage is applied from the gel peeling power source to the working electrode wherein (A) illustrates the cross section when a positive voltage is applied and (B) illustrates the cross section when a negative voltage is applied.

Next, the following section will describe a mechanism to apply positive and negative voltages alternately to the working electrode 13 to thereby peel the gel 2 completely from the working electrode 13. FIG. 7 shows a cross-sectional view illustrating the working electrode 13, the pattern 3 that is composed of conductive polymer and the gel when a voltage is applied from the gel peeling power source 27 to the working electrode 13. FIG. 7(A) illustrates the cross section when a positive voltage is applied. FIG. 7(B) illustrates the cross section when a negative voltage is applied. As shown in FIG. 7(A), the pattern 3 that is composed of conductive polymer is formed while negative ions in the electrolyte aqueous solution 11A are being doped. In this status, the pattern 3 that is composed of conductive polymer is swollen. When a negative voltage is applied to the working electrode 13 after the electropolymerization on the other hand, undoping is occurred as shown in FIG. 7(B), thus causing the shrinkage of the pattern 3 that is composed of conductive polymer. When a positive voltage is applied to the working electrode 13 on the other hand, negative ions are doped again, thus causing the swelling of the pattern 3 that is composed of conductive polymer (see FIG. 7(A)).

Furthermore, since the gel 2 is flexible, the gel 2 can shrink in accordance with the shrinkage of the pattern 3 that is composed of conductive polymer on the working electrode 13. Through the series of shrinkage motions, a force is generated between the pattern 3 that is composed of conductive polymer and the working electrode 13, thus the pattern 3 that is composed of conductive polymer is completely peeled from the surface of the working electrode 13. As a result, the pattern 3 that is composed of conductive polymer can be transferred onto the surface of the gel 2.

The method of peeling the gel 2 as shown in FIG. 2(D) and FIG. 7 uses a volume change caused by the doping or undoping reaction of the dopant included in the conductive polymer. The above-described method of peeling the gel 2 is a reversible reaction that can be controlled by applying an appropriate voltage via the working electrode 13 to the pattern 3 that is composed of conductive polymer and that is formed on the gel 2. The peeling of the gel 2 can be controlled based on the type of the dopant used for the electrolyte liquid 11, the electrolysis current during electropolymerization, the current application time, or the number of voltage applications after the electropolymerization by the gel peeling power source 27 for example.

According to the method of manufacturing the porous structure 1 provided with a pattern that is composed of conductive polymer of the present invention, the pattern 3 consisting of a thin film of conductive polymer can be formed on the gel 2 by using the electropolymerization and the electrode pattern 25 formed on the working electrode 13 used for the electropolymerization. The form of the thickness of the pattern 3 that is composed of conductive polymer transferred to the gel 2 from the electrode pattern 25 formed on the working electrode 13 can be controlled electrically by the use of the electropolymerization. Thus, by a simple and electrically-controllable method such as electropolymerization of conductive polymer as well as doping and undoping, the conductive polymer pattern 3 can be formed even on the surface of the soft gel 2 including water at a high water content percentage for example. According to this manufacturing method, w the pattern 3 that is composed of conductive polymer can be selectively formed only on the working electrode 13. Thus, this is also a useful method to coat the gel 2 with conductive polymer in particular.

Example 1

The following section will describe an Example of the present invention in more detail.

First, the following section will describe the working electrode 13, the counter electrode 14, and the reference electrode 15 used for the electropolymerization apparatus 10 as shown in FIG. 3 and FIG. 4.

(Working Electrode)

The working electrode 13 was prepared by using a slide glass as the substrate 19 to prepare, then the electrode pattern 25 composed of platinum (Pt) is fabricated on the substrate 19 by based on a series of semiconductor microfabrication techniques as shown below.

For the electrode pattern 25 as shown in FIG. 5, a mask was prepared using an emulsion mask (2 inches, made by KONICA MINOLTA) and a laser drawing apparatus (made by Heiderberg Instruments). The electrode pattern 25 was prepared using drawing preparation software (AutoCAD2009 made by Autodesk) and was used as data for the laser drawing apparatus.

The substrate 19 was coted with a positive photoresist (AZ1500, 38 cp, made by AZ Electronic Materials) by spin coating (4000 rpm, 30 sec). Then, the coated positive photoresist was prebaked (100 degrees Centigrade (V), 10 min).

Next, the slide glass 19 covered by the positive photoresist was exposed with the mask by an ultraviolet exposure apparatus.

Next, the exposed positive photoresist was processed by development liquid and was washed with distilled water (30 sec×2) and was post-baked at 100° C. for 10 minutes, thereby forming a positive photoresist pattern.

After the preparation of the resist pattern, some resist may remain in a region on the slide glass 19 in which no resist pattern is formed. In such a case, an oxygen plasma (100 W, 2 minutes) was processed by using a plasma ashing apparatus (LTA101, made by Yanaco) to thereby remove the unnecessary resist remaining on the surface of the substrate 19.

Next, Titanium (Ti) of a thickness of 5 nm and Pt of a thickness of 50 to 300 nm were deposited in this order to form an electrode layer onto the substrate 19 having the positive photoresist pattern thereon by using a sputtering deposition apparatus (L-350S-C, made by ANELVA).

Finally, the substrate 19 having the deposited electrode layer thereon was subjected to a 15-minute ultrasonic cleaning using acetone, 86% ethanol, isopropyl alcohol, and distilled water in this order to thereby cause the photoresist to be lifted off. As a result, the metal layer deposited on the positive photoresist pattern was removed. In this manner, the working electrode 13 including the electrode pattern 25 composed of Pt was prepared on the surface of the substrate 19.

(Counter Electrode)

The counter electrode 14 was prepared by a flat plate electrode made of Pt.

(Reference Electrode)

As the reference electrode 15, a silver/silver chloride electrode, which can generate a potential with high reproducibility, can be prepared and handled easily, and can have a compact shape, was used. The silver/silver chloride electrode was formed by depositing silver chloride on the surface of a silver wire. This reference electrode 15 will be represented as Ag/AgCl.

(Preparation of Container and Agarose Gel)

First, the container 12 was fixed on the substrate 19 of the working electrode 13. The container 12 was prepared by a silicone sheet having a thickness of 2 mm. This container 12 has no bottom.

Next, the agarose solution of 2.8 weight % (wt %) was prepared by adding electrophoresis agarose powders (made by Wako Pure Chemical Industries, Ltd.) into the ion-exchange water. The agarose solution was heated to boil using a microwave oven (500 W) so that the agarose solution has a sol-like status. Then, the sol-like solution was poured into the container 12 made by the silicone sheet and was left until to be cooled to the room temperature thereby causing the sol-like solution to turn to gel. In this manner, the agarose gel 2A having a predetermined shape was prepared.

(Electrolyte Aqueous Solution 11A and Electropolymerization)

The electrolyte aqueous solution 11A was prepared by mixing 50 mM (millimole) of 3, 4 ethylenedioxythiophene (also called EDOT, made by Sigma) with a dopant of 100 mM of potassium nitrate ($KNO_3$, made by Wako Pure Chemical Industries, Ltd.).

Based on the reference electrode 15 as a reference, the voltage of 1.0V as the electropolymerization potential was applied to the electrolyte aqueous solution 11A. The status, in which the reference electrode 15 is Ag/AgCl as described above and the electropolymerization potential is 1.0V, will be represented by +1.0V Ag/AgCl. The electropolymerization was carried out for the time from 10 to 60 minutes.

(Porous Structure 1 Provided with Pattern 3 that is Composed of Conductive Polymer)

After the above electropolymerization, the following peeling was performed to prepare the porous structure 1 provided with the pattern 3 that is composed of various conductive polymers.

After the electropolymerization, −0.5V Ag/AgCl was applied for one minute. Then, +0.5V Ag/AgCl was applied for one minute. This operation was repeated several times. Then, the electropolymerization solution was removed and the agarose gel 2A was rinsed with the distilled water. Finally, the chamber was removed and then the agarose gel 2A was peeled by tweezers from the substrate 19 of the working electrode 13.

FIG. 8(A) is an optical image of the porous structure 1 provided with a line pattern composed of the conductive polymer of Example 1 formed by the electropolymerization followed by three cycles of the application of positive and negative voltages and (B) is a schematic view of the image. As can be seen from FIG. 8, the black PEDOT pattern part is transferred to the agarose gel 2A i.e. the pattern part composed of a large area of PEDOT is transferred to the agarose gel 2A. Hereinafter, the PEDOT pattern part is called a PEDOT electrode 3A.

FIG. 9(A) illustrates an expanded optical image of a grid-like line pattern composed of conductive polymer of FIG. 8, (B) is a schematic view of the image and (C) illustrates an expanded optical image of (A). As can be seen from FIG. 9, the grid-like pattern having a line width of 25 μm is transferred to the agarose gel 2A without being broken. Thus, the pattern of the PEDOT electrode 3A having a narrow line width and a high line density (i.e., a dense pattern of the PEDOT electrode 3A) is transferred to the agarose gel 2A.

(Dependency of the Dopant Added to PEDOT)

When the electrode pattern 25 of the working electrode 13 is transferred to the agarose gel 2A, the transfer success rate was different depending on the type of the dopant used in the electropolymerization solution, the electropolymerization time, and the number of voltage applications after the electropolymerization.

(Electrolyte Aqueous Solution 11A Added with PSS)

In order to make comparison among dopants, the electrolyte aqueous solution 11A composed of 50 mM of EDOT and 2 mM of sodium polystyrenesulfonate (NaPSS) was prepared. NaPSS is used for the dopant for PEDOT dispersion liquidused. The electropolymerization potential is +1V Ag/AgCl and the electropolymerization time is 60 minutes. After the electropolymerization, an alternate application of −0.5V for one minute and +0.5V for one minute was repeated three times for the purpose of peeling.

Figure 10:
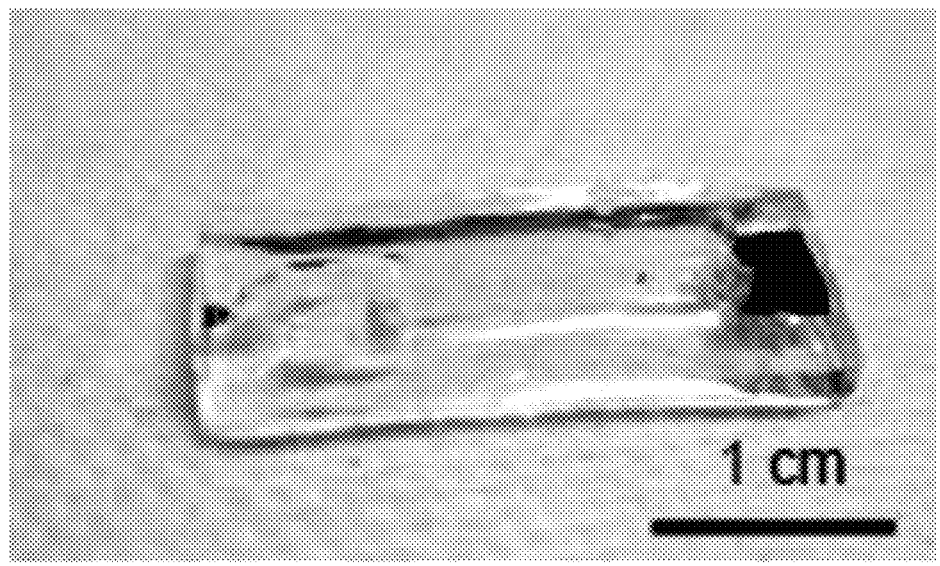
FIG. 10 illustrates the result of the transfer using PSS as a dopant.

PSS is characterized as follows that its chemical stability is high, PEDOT film polymerized with an addition of PSS has a lower electrical conductivity than that obtained by a $KNO_3$ dopant and PSS has a very-high molecular weight of 70,000. However, as shown in FIG. 10, the result of the transfer using PSS as a dopant shows that the PEDOT electrode 3A was not peeled from the working electrode 13 and the agarose gel 2A was broken, even when the electropolymerization was performed under the same conditions as those of $KNO_3$. This is presumably considered due to that the PSS has a very-high molecular weight and thus the PSS could not be undoped from the doped status during polymerization, thus failing to obtain a sufficient volume change.

Next, a comparison was made with regard to a difference depending on the electropolymerization time and the number of the volume change after the electropolymerization. The dopant was 100 mM of $KNO_3$ and the electropolymerization was performed at 1.0V. Different electropolymerization times of 10 minutes, 15 minutes, 20 minutes, 30 minutes, and 60 minutes were used and different voltage application numbers after the electropolymerization of 1, 2, and 3 were used. Under these different conditions, how the transfer was different was confirmed.

FIG. 11 illustrate the porous structure 1 including the pattern 3 that is composed of conductive polymer wherein (A) illustrates the transfer when the electropolymerization time is 10 minutes and (B) illustrates the transfer when the electropolymerization time is 60 minutes. As can be seen from FIG. 11, the electropolymerization time of 10 minutes cannot provide a complete transfer while the electropolymerization time of 60 minutes can provide a complete transfer.

Figure 12:
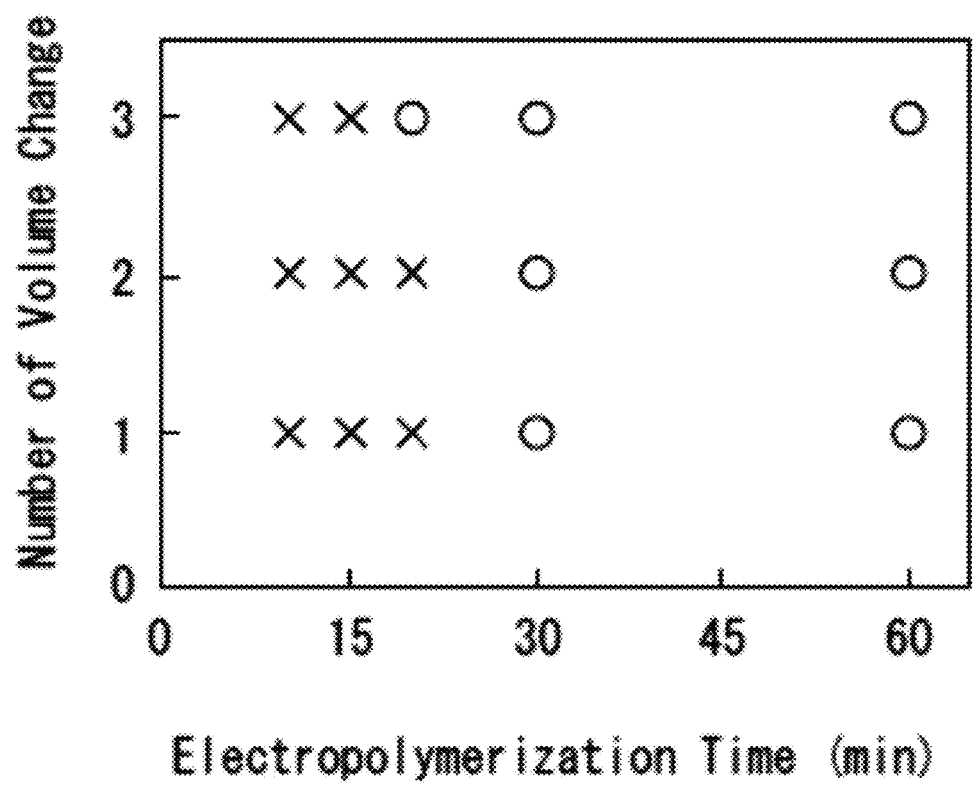
FIG. 12 illustrates the relation between the electropolymerization time and the volume change number of the peeling step.

FIG. 12 illustrates the relation between the electropolymerization time and the volume change number of the peeling step. In FIG. 12, the horizontal axis shows the electropolymerization time (minute). As can be seen from FIG. 12, the electropolymerization time of 30 minutes or more provides a successful transfer regardless of the volume change number. Such a long electropolymerization time means a high amount of electropolymerized PEDOT electrode 3A and thus presumably means a proportionally increased volume change amount during doping and undoping. As can be seen from the above, in order to peel the PEDOT electrode 3A from the pattern 25 of the working electrode 13, the size of expansion and contraction is more important than the number of expansion and contraction.

(Electrical Stimulation of the Cell by PEDOT Electrode 3A)

The porous structure 1 provided with the pattern 3 that is composed of conductive polymer was used to perform the electrical stimulation to myotube cells.

(Myotube Cell Gel Sheet)

Figure 13:
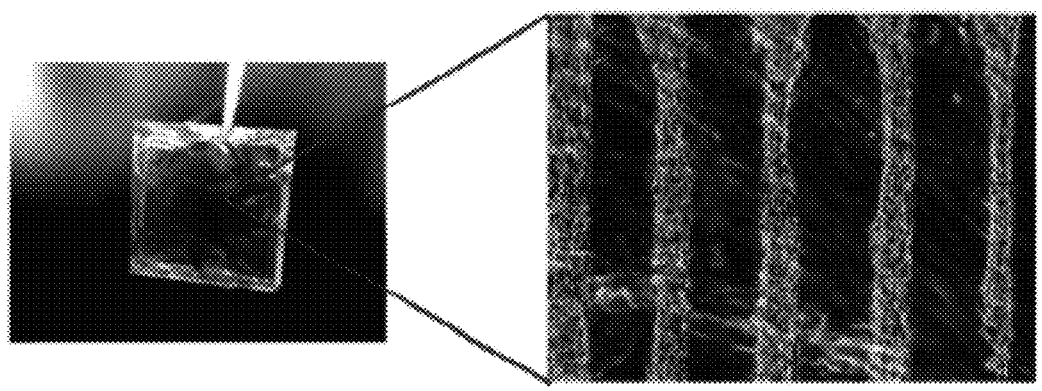
FIG. 13 illustrates a myotube cell gel sheet photograph and a transferred pattern of cells.

A myotube cell gel sheet was prepared to be combined with the porous structure 1 provided with the pattern 3 that is composed of conductive polymer. This myotube cell gel sheet was obtained by transferring a myotube cell pattern to fibrin gel in order to maintain the shrinkage motion of the myotube cells and the pattern structure for a long period. Fibrin gel is a main component of blood clot and is hydrogel 2A composed of fibrin obtained by the polymerization of fibrinogen. The fibrin gel can be easily prepared by mixing thrombin as bridging material into fibrinogen. The fibrin gel is the hydrogel 2A obtained by chemical crosslink and has a mesh structure. FIG. 13 illustrates a photograph of the myotube cell gel sheet and the transferred cell pattern.

Figure 14:
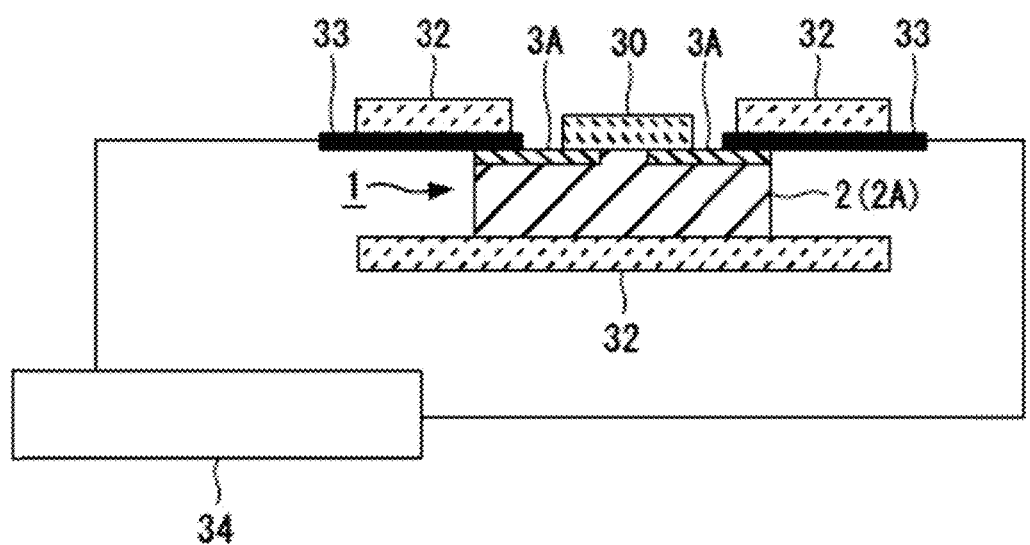
FIG. 14 is a schematic view illustrating the electrical stimulation of myotube cells using a porous structure provided with a pattern that is composed of conductive polymer.

FIG. 14 is a schematic view illustrating the electrical stimulation to myotube cells using the porous structure 1 provided with the pattern 3 that is composed of conductive polymer. As shown in FIG. 14, the porous structure 1 provided with the pattern 3 that is composed of conductive polymer is placed on an acrylic plate 32. The myotube cell gel sheet 30 is placed on the PEDOT electrodes 3A formed on the agarose gel 2A thereon. The PEDOT electrodes 3A are arranged with an interval therebetween of 400 µm. A Pt electrode 33 was used to provide an electrical contact (i.e., contact) between an electrical stimulation apparatus 34 and the PEDOT electrode 3A. Hence, the myotube cell gel sheet 30 was set so as not to be directly contacted to the Pt electrode 33.

Here, the acrylic plates 32 are placed on left and right ends of the PEDOT electrode 3A having no contact with the myotube cell gel sheet 30. Specifically, the pattern 3 that is composed of conductive polymer and the Pt electrode 33 is sandwiched between the acrylic plate 32 at the upper part of the Pt electrodes and the acrylic plate 32 thereby maintaining an electrical contact having thereon the pattern 3 that is composed of conductive polymer is provided on the acrylic plate 32, thereby maintaining an electrical contact.

The myotube cell gel sheet 30 was stimulated electrically by using the electrical stimulation apparatus (SEN-7203 made by NIHON KOHDEN) 34 and the isolator (SS-202J made by NIHON KOHDEN). The electrical stimulation by pulse was performed by the conditions that the application voltage of 6V, the application time of 600 msec and an interval of 1 second.

Comparative Example

As a Comparative Example, agarose gel 2A was prepared that has a direct contact with the Pt electrode 33 without provided with the PEDOT electrode 3A therebetween.

Figure 15:
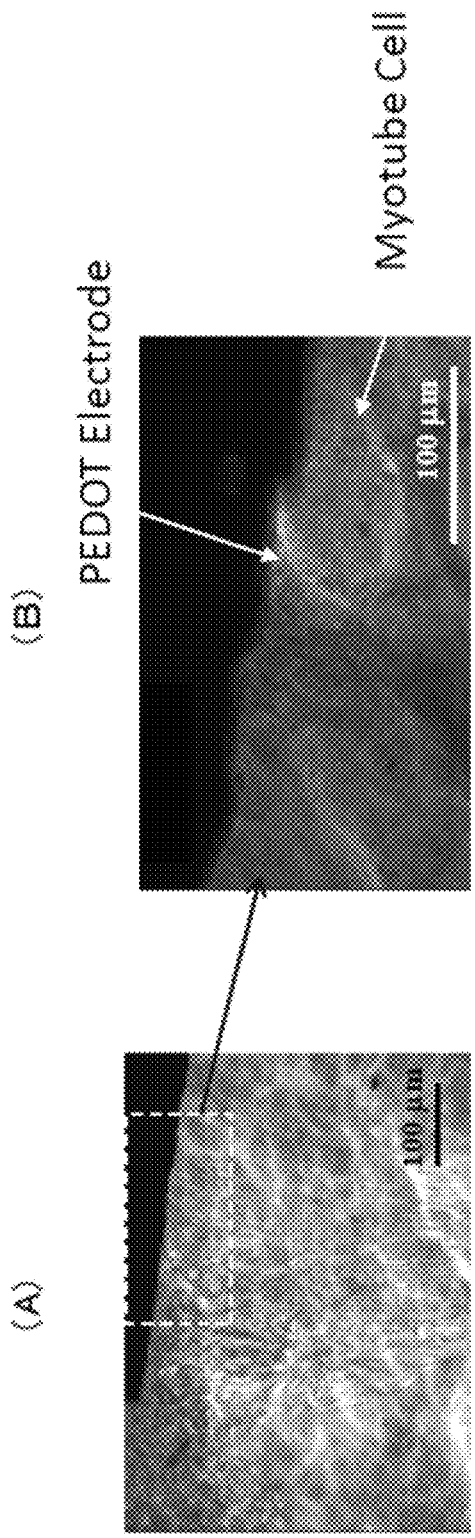
FIG. 15 illustrate the electrical stimulation of a myotube cell gel sheet observed by an optical microscope wherein (A) illustrates a myotube cell gel sheet and (B) illustrates a contact section of the myotube cell gel sheet and a PEDOT electrode.

FIG. 15 illustrates the electrical stimulation of the myotube cell gel sheet 30 observed by an optical microscope wherein (A) illustrates the myotube cell gel sheet 30 and (B) illustrates the contact section at which the myotube cell gel sheet 30 has a contact with the PEDOT electrode 3A, respectively.

As can be seen from FIG. 15(A), the voltage application causes the contraction motion of the surrounded myotube cell gel sheet 30, thus showing that the PEDOT electrode 3A formed on the gel 2 can be used to electrically stimulate the myotube cell gel sheet 30.

As can be seen from the expanded view of FIG. 15(B) showing the neighborhood of the PEDOT electrode 3A, the contraction motion of the myotube cell gel sheet 30 causes the shrinkage of the PEDOT electrode 3A itself. Since thehe reason is that the PEDOT electrode 3A is composed only by the flexible agarose gel 2A and the PEDOT 3A, this is not impossible in the case of a conventional electrode substrate.

Furthermore, when the electrical stimulation was performed only by the agarose gel 2A as the Comparative Example, little contraction motion was observed. This is presumably caused by the formation of an electric field in the entire agarose gel 2A by the Pt electrode 33 for contact. However, this contraction motion was very little and was clearly different from the case of the agarose gel 2A to which the PEDOT electrode 3A was transferred. Furthermore, since the Pt electrode 33 for contact provides a small interfacial capacity, electrolyzation was caused at the contact part between the Pt electrode 33 and the agarose gel 2A, thus causing bubbles. A continued observation showed that the generated bubbles pushed up the myotube cell gel sheet 30.

As can be seen from the above, the combination of the agarose gel 2A to which the PEDOT electrode 3A is transferred and the myotube cell gel sheet 30 can provide the electrical stimulation to the myotube cell gel sheet 30. It was confirmed that the myotube cell gel sheet 30 performs the contraction motion repeatedly in accordance with an electrical stimulation and the PEDOT electrode 3A itself also shrinks in synchronization with the myotube cell gel sheet 30. On the other hand, the agarose gel 2A to which no PEDOT electrode 3A was transferred showed electrolyzation and bubbles generated thereon. In the case of the PEDOT electrode 3A and the myotube cell gel sheet 30 of Example 1, no such bubbles were found, thus demonstrating that the PEDOT electrode 3A is an electrode that provides a superior electrical stimulation to the myotube cell gel sheet 30.

Example 2

The porous structure 1 provided with a pattern that is composed of conductive polymer of Example 2 was prepared as same manner in Example 1, except for that the agarose gel 2A was composed of collagen. As the pattern 3 that is composed of conductive polymer, the PEDOT electrode 3A was used. Myotube cells could be activated by the electrical stimulation as same as in that of Example 1.

FIG. 16(A) illustrates an optical image of the porous structure 1 provided with a pattern that is composed of conductive polymer of Example 2 and (B) is a schematic view of the image. As can be seen from FIG. 16, the PEDOT electrode 3A composed of the black PEDOT pattern part is transferred to collagen without being broken.

Example 3

The porous structure 1 provided with a pattern that is composed of conductive polymer of Example 3 was prepared as same manner in Example 1, except for that the agarose gel 2A was composed of glucomannan. As the pattern 3 that is composed of conductive polymer, the PEDOT electrode 3A was used. Myotube cells could be activated by the electrical stimulation as same as in that of Example 1.

FIG. 17(A) illustrates an optical image of the porous structure 1 provided with a pattern that is composed of conductive polymer of Example 3, and (B) is a schematic view of the image. As can be seen from FIG. 17, the PEDOT electrode 3A composed of the black PEDOT pattern part is transferred to glucomannan without being broken.

Example 4

The porous structure 1 provided with a pattern that is composed of conductive polymer of Example 4 was prepared as same manner in Example 1, except for that the agarose gel 2A was composed of polyacrylamide. As the pattern 3 that is composed of conductive polymer, the PEDOT electrode 3A was used. Myotube cells could be activated by the to an electrical stimulation as same as in that of Example 1.

FIG. 18(A) illustrates an optical image of the porous structure 1 provided with a pattern that is composed of conductive polymer of Example 4, and (B) is a schematic view of the image. As can be seen from FIG. 18, the PEDOT electrode 3A composed of the black PEDOT pattern part is transferred to polyacrylamide without being broken.

The present invention is not limited to the Examples mentioned above. Various modifications are possible within the scope of claims. Such modifications are also included in the scope of the present invention.

INDUSTRIAL APPLICABILITY

The porous structure provided with a pattern that is composed of conductive polymer of the present invention is excellent biocomapatibility. This porous structure can be applied to many fields such as a flexible electrode pad, for a cell culture base in the biomedical field, a cell stimulation system that is stretchable in synchronization with cells or tissue, a biosensor, or a polymer actuator etc. for example.

What is claimed is:

1. An electrode, comprising:
   a porous body made of gel; and
   a pattern that is composed of conductive polymer provided only on the porous body, wherein the gel is composed of hydrogel, and
   wherein the pattern that is composed of conductive polymer is contacted to cells or tissue.

2. The electrode according to claim 1, wherein the hydrogel includes water at a water content percentage of 70 to 99%.

3. The electrode according to claim 1, wherein the hydrogel is any of agarose gel, collagen, glucomannan, polyacrylamide, polyvinyl alcohol, polyhydroxyethyl methacrylate, or polyvinylpyrrolidone.

4. The electrode according to claim 1, wherein the conductive polymer is any of PEDOT, polypyrrole, or polyacetylene.

5. The electrode according to claim 1, wherein the conductive polymer is added with a dopant.

6. The electrode according to claim 1, wherein the conductive polymer has a conductivity of 10 S/cm or more.

7. A method of manufacturing the electrode according to claim 1, comprising:
   a step of forming an electrode pattern functioning as a working electrode;
   a step of inserting the working electrode pattern to electrolyte liquid including raw material of conductive polymer;
   a step of placing a porous body on the working electrode pattern;
   a step of performing electropolymerization for a predetermined time to deposit a pattern that is composed of conductive polymer between the porous body and the electrode pattern; and
   a step of peeling the porous body from the electrode pattern to thereby obtain a porous structure provided with a pattern that is composed of conductive polymer.

8. The method of manufacturing the electrode according to claim 7, wherein the raw material of conductive polymer is monomer of the conductive polymer.

9. The method of manufacturing the electrode according to claim 7, wherein the electropolymerization is followed by at least one or more applications of negative and positive voltages to the working electrode in an alternate manner.

10. The method of manufacturing the electrode according to claim 7, wherein the electrolyte liquid further includes a dopant.

11. The method of manufacturing the electrode according to claim 10, wherein $KNO_3$ is used as the dopant.

12. The method of manufacturing the electrode according to claim 7, wherein the pattern that is composed of conductive polymer has the minimum line width that is wider than the minimum line width of the electrode pattern functioning as a working electrode by 1 µm to 10 µm.

13. The method of manufacturing the electrode according to claim 7, wherein the hydrogel is any of agarose gel, collagen, glucomannan, polyacrylamide, polyvinyl alcohol, polyhydroxyethyl methacrylate, or polyvinylpyrrolidone.

* * * * *